(12) United States Patent
Gee

(10) Patent No.: US 11,845,717 B1
(45) Date of Patent: Dec. 19, 2023

(54) ISOMERIZATION OF LINEAR OLEFINS WITH SOLID ACID CATALYSTS AND PRIMARY ESTERS

(71) Applicant: Chevron Phillips Chemical Company LP, The Woodlands, TX (US)

(72) Inventor: Jeffery C. Gee, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 0 days.

(21) Appl. No.: 17/894,212

(22) Filed: Aug. 24, 2022

(51) Int. Cl.
*C07C 5/25* (2006.01)
*B01J 31/10* (2006.01)
*C07C 11/02* (2006.01)

(52) U.S. Cl.
CPC ............. *C07C 5/2568* (2013.01); *B01J 31/10* (2013.01); *C07C 11/02* (2013.01); *B01J 2231/52* (2013.01); *C07C 2531/10* (2013.01)

(58) Field of Classification Search
None
See application file for complete search history.

(56) References Cited

U.S. PATENT DOCUMENTS

| 3,631,218 A | * | 12/1971 | Carter | ................... C07C 5/2593 502/154 |
| --- | --- | --- | --- | --- |
| 6,479,440 B1 | | 11/2002 | Le Coent | |
| 7,332,637 B2 | | 2/2008 | Gee | |
| 7,655,827 B2 | | 2/2010 | Ching | |
| 8,043,991 B2 | | 10/2011 | Ching | |
| 8,293,698 B2 | | 10/2012 | Le Coent | |
| 2004/0249229 A1 | * | 12/2004 | Gee | ........................ C07C 5/2568 585/671 |
| 2009/0163757 A1 | * | 6/2009 | Gee | ........................ C07C 5/2518 585/671 |

FOREIGN PATENT DOCUMENTS

| WO | 2020222168 A1 | 11/2020 |
| --- | --- | --- |
| WO | 2020222171 A1 | 11/2020 |

OTHER PUBLICATIONS

Jeffrey C. Gee, et al., "A Kinetic and Mechanistic Study of the Double Bond and Skeletal Isomerization of 1-Tetradecene on SAPO-11," Elsevier B.V., Applied Catalysis A: General, vol. 362, Mar. 17, 2009, 11 pp.

* cited by examiner

*Primary Examiner* — Renee Robinson
*Assistant Examiner* — Alyssa L Cepluch
(74) *Attorney, Agent, or Firm* — Merchant & Gould P.C.

(57) ABSTRACT

Isomerized olefin products are produced by contacting an olefin feed containing a $C_{10}$ to $C_{20}$ normal alpha olefin, a solid acid catalyst, and a $C_2$ to $C_{15}$ primary ester to form the isomerized olefin product. Typical primary esters used in the processes include formates and acetates. Linear olefin compositions are produced that contain at least 80 wt. % $C_{10}$ to $C_{20}$ linear internal olefins, less than 8 wt. % $C_{10}$ to $C_{20}$ normal alpha olefins, less than 8 wt. % dimers of $C_{10}$ to $C_{20}$ olefins, less than 15 wt. % $C_{10}$ to $C_{20}$ branched olefins, and at least 1 wt. % $C_2$ to $C_{15}$ primary ester and less than 8 wt. % secondary esters.

21 Claims, No Drawings

ISOMERIZATION OF LINEAR OLEFINS WITH SOLID ACID CATALYSTS AND PRIMARY ESTERS

FIELD OF THE INVENTION

The present disclosure concerns processes for producing an isomerized olefin product. More particularly, the present disclosure relates to producing the isomerized olefin product by contacting a normal alpha olefin feed, a solid acid catalyst, and a primary ester.

BACKGROUND OF THE INVENTION

Various catalysts can be used to promote the double bond isomerization of linear olefins. However, these catalysts also promote at least one undesirable simultaneous reaction, either skeletal isomerization of the linear olefin, or dimerization of the linear olefin, or both of these reactions. It would be beneficial to develop isomerization processes that can produce an isomerized product with low levels of dimer, low levels of branched olefins, and a nearly equilibrium distribution of linear double bond isomers. Accordingly, it is these ends that the present invention is generally directed.

SUMMARY OF THE INVENTION

This summary is provided to introduce a selection of concepts in a simplified form that are further described below in the detailed description. This summary is not intended to identify required or essential features of the claimed subject matter. Nor is this summary intended to be used to limit the scope of the claimed subject matter.

Processes for isomerizing olefins are disclosed herein. These processes can comprise contacting (i) an olefin feed comprising a $C_{10}$ to $C_{20}$ normal alpha olefin, (ii) a solid acid catalyst, and (iii) a $C_2$ to $C_{15}$ primary ester to form an isomerized olefin reaction product. The olefin feed (containing the normal alpha olefin), the solid acid catalyst, and the primary ester can be contacted in any order or sequence.

Linear internal olefin compositions also are provided herein. Such compositions can comprise (a) at least 80 wt. % $C_{10}$ to $C_{20}$ linear internal olefins, (b) less than or equal to 8 wt. % $C_{10}$ to $C_{20}$ normal alpha olefins, (c) less than or equal to 8 wt. % dimers of $C_{10}$ to $C_{20}$ olefins, (d) less than or equal to 15 wt. % $C_{10}$ to $C_{20}$ branched olefins, (e) and at least 1 wt. % $C_2$ to $C_{15}$ primary ester and less than or equal to 8 wt. % secondary esters.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features can be envisioned. For each and every aspect and/or feature disclosed herein, all combinations that do not detrimentally affect the systems, compositions, processes, and/or methods described herein are contemplated with or without explicit description of the particular combination. Additionally, unless explicitly recited otherwise, any aspect and/or feature disclosed herein can be combined to describe conceived systems, compositions, processes, and/or methods consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise. The terms "a," "an," and "the" are intended to include plural alternatives, e.g., at least one, unless otherwise specified. For instance, the disclosure of "a normal alpha olefin" or "a solid acid catalyst" is meant to encompass one, or mixtures or combinations of more than one, normal alpha olefin or solid acid catalyst, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique. Herein, "contacting" or "combining" two or more components can result in a reaction product.

The term "hydrocarbon" refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon). The term "alkane" refers to a saturated hydrocarbon compound.

The term "olefin" refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has 1) a carbon-carbon double bond between the first and second carbon atom of the longest contiguous chain of carbon atoms, and 2) at least one hydrogen atom bound to the second carbon of the chain. The term "alpha olefin" includes linear and branched alpha olefins and alpha olefins which can have more than one non-aromatic carbon-carbon double bond, unless expressly stated otherwise. In the case of branched olefins, a branch can be at the 2-position of a 1-alkene (a vinylidene) with respect to the olefin double bond. Thus, the term "vinylidene" refers to a 1-alkene having an alkyl branch at the 2-position with respect to the olefin double bond. The term "normal alpha olefin" refers to a linear aliphatic hydrocarbon mono-olefin having 1) a carbon-carbon double bond between the first and second carbon atoms, and 2) at least one hydrogen atom bound to the second carbon of the chain. The term "linear internal olefin" refers to a linear aliphatic hydrocarbon mono-olefin having a double bond that is not between the first and second carbon atoms.

Features within this disclosure that are provided as minimum values can be alternatively stated as "at least" or "greater than or equal to" any recited minimum value for the feature disclosed herein. Features within this disclosure that are provided as maximum values can be alternatively stated as "less than or equal to" or "below" any recited maximum value for the feature disclosed herein.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, there can be a range of weight ratios of the olefin feed to the solid acid catalyst in aspects of this invention. By a disclosure that weight ratio is in a range from 1:1 to 100:1, the intent is to recite that the weight ratio can be any amount in the range and, for example, can include any range or combination of ranges from 1:1 to 100:1, such as from 1:1 to 10:1, from 1.5:1 to 40:1, or from 4:1 to 20:1, and so forth. Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods and materials similar or equivalent to those described herein can be used in the practice or testing of the processes and reaction systems, the typical methods and materials are herein described.

All publications and patents mentioned herein are incorporated herein by reference in their entirety for the purpose of describing and disclosing, for example, the constructs and methodologies that are described in the publications and patents, which might be used in connection with the present disclosure.

DETAILED DESCRIPTION OF THE INVENTION

Disclosed are processes for isomerizing olefins, and specifically, processes for isomerizing normal alpha olefins. Advantageously, the disclosed processes can achieve the desired equilibrium double bond distribution while concurrently minimizing both dimerization and skeletal isomerization of the normal alpha olefin.

Herein, the isomerization process can comprise contacting the normal alpha olefin feed with a solid acid catalyst and a primary ester, in which the primary ester unexpectedly suppresses both olefin dimerization and skeletal isomerization, without significantly impacting olefin double bond isomerization. Beneficially, the primary ester can be easily removed from the isomerized olefin product stream using conventional distillation or a related technique, and then recycled if desired.

Isomerizing Olefins

The processes for isomerizing olefins disclosed herein can comprise (or consist essentially of, or consist of) contacting (i) an olefin feed comprising a $C_{10}$ to $C_{20}$ normal alpha olefin, (ii) a solid acid catalyst, and (iii) a $C_2$ to $C_{15}$ primary ester to form an isomerized olefin reaction product. Generally, the features of the processes (e.g., the olefin feed, the normal alpha olefin, the solid acid catalyst, the primary ester, and the reaction conditions under which the isomerized olefin reaction product is formed, among others) are independently described herein, and these features can be combined in any combination to further describe the disclosed processes. Moreover, additional process steps can be performed before, during, and/or after any of the steps of any of the processes disclosed herein, unless stated otherwise. Further, isomerized olefin reaction products and linear internal olefin products produced by any of the disclosed processes also are encompassed herein.

The olefin feed to the isomerization process comprises a $C_{10}$ to $C_{20}$ normal alpha olefin. In one aspect, the olefin feed can comprise a $C_{12}$ to $C_{20}$ normal alpha olefin, while in another aspect, the olefin feed can comprise a $C_{14}$ to $C_{18}$ normal alpha olefin, and in yet another aspect, the olefin feed can comprise a $C_{16}$ to Cis normal alpha olefin. For instance, the olefin feed can comprise (or consist essentially of, or consist of) 1-decene, 1-dodecene, 1-tetradecene, 1-hexadecene, 1-octadecene, or any combination thereof, alternatively, 1-decene; alternatively, 1-dodecene; alternatively, 1-tetradecene; alternatively, 1-hexadecene; or alternatively, 1-octadecene. Thus, mixtures of various normal alpha olefins having different numbers of carbon atoms can be used, or normal alpha olefins having predominantly a single number of carbon atoms can be used.

Any suitable amount of the olefin feed can be the normal alpha olefin. Generally, the olefin feed contains at least 15 wt. % of $C_{10}$ to $C_{20}$ normal alpha olefins, and more often, contains at least 50 wt. %, at least 70 wt. %, at least 80 wt. %, at least 85 wt. %, at least 90 wt. %, at least 92.5 wt. %, or at least 95 wt. % of $C_{10}$ to $C_{20}$ normal alpha olefins, and in some aspects, less than or equal to 99 wt. %, less than or equal to 97 wt. %, less than or equal to 95 wt. %, or less than or equal to 92 wt. % of $C_{10}$ to $C_{20}$ normal alpha olefins, and in other aspects, a range from any minimum amount disclosed herein to any maximum amount disclosed herein of $C_{10}$ to $C_{20}$ normal alpha olefins. Likewise, the olefin feed can contain these same minimum amounts, maximum amounts, and ranges for any combination of single carbon numbered normal alpha olefins described herein; or alternatively, of any single carbon numbered normal alpha olefin described herein. For instance, in a non-limiting example, the olefin feed can comprise at least 50 wt. %, at least 60 wt. %, at least 70 wt. %, at least 80 wt. %, at least 85 wt. %, at least 90 wt. %, or at least 95 wt. %, and less than or equal to 99 wt. %, less than or equal to 97 wt. %, less than or equal to 95 wt. %, or less than or equal to 92 wt. % (e.g., a range from any minimum amount disclosed herein to any maximum amount disclosed herein, such as from 85 wt. % to 95 wt. % or from 90 wt. % to 99 wt. %) of 1-decene; alternatively, 1-dodecene; alternatively, 1-tetradecene; alternatively, 1-hexadecene; or alternatively, 1-octadecene. Thus, mixtures of various normal alpha olefins having different numbers of carbon atoms can be present in the olefin feed, or normal alpha olefins having predominantly a single number of carbon atoms can be present in the olefin feed. While a mixture of different carbon number olefins can be present in the olefin feed, the processes disclosed herein are particularly well suited for use with olefin feeds having a single carbon number.

In addition to normal alpha olefins, the olefin feed also can contain branched olefins, but typically the branched olefin content is a minor fraction of the olefin feed. Often, the branched olefins—in which the branch (or branches) can be at any position on the branched olefins—constitute less than or equal to 12 wt. % of the olefin feed, but at least 0.5 wt. %, at least 1 wt. %, at least 2 wt. %, or at least 4 wt. %. In one aspect, for instance, the olefin feed contains less than or equal to 10 wt. % branched olefins, and in another aspect, the olefin feed contains less than or equal to 8 wt. % branched olefins, and in yet another aspect, the olefin feed contains less than or equal to 6 wt. % branched olefins, and in still another aspect, the olefin feed contains less than or equal to 5 wt. % branched olefins. The olefin feed can contain any amount of branched olefins between these respective minimum and maximum amounts, such as from 0.5 to 12 wt. %, from 4 to 12 wt. %, from 1 to 10 wt. %, from 4 to 10 wt. %, from 0.5 to 8 wt. %, from 1 to 6 wt. %, or from 0.5 to 5 wt. %, and the like.

The $C_2$ to $C_{15}$ primary ester used in the isomerization process is not particularly limited, and herein, a primary ester means that the carbon atom of the alkyl group bound to the ester group must have at least 2 hydrogen atoms. The primary ester can be a $C_2$ to $C_{10}$ primary ester or a $C_3$ to $C_{15}$ primary ester in some aspects, while the primary ester can be a $C_4$ to $C_{15}$ primary ester or a $C_4$ to $C_{10}$ primary ester in other aspects. Representative and non-limiting examples of primary esters that can be used in the isomerization processes disclosed herein include methyl acetate, ethyl acetate, n-propyl acetate, n-butyl acetate, pentyl acetate, isoamyl acetate, hexyl acetate, heptyl acetate, octyl acetate, nonyl acetate, decyl acetate, and the like, as well as any combination thereof. Other representative and non-limiting examples of primary esters that can be used in the isomerization processes disclosed herein include methyl formate, ethyl formate, n-propyl formate, n-butyl formate, pentyl formate, isoamyl formate, hexyl formate, heptyl formate, octyl formate, nonyl formate, decyl formate, and the like, as well as any combination thereof. The primary ester is not limited solely to those acetates and formates listed above. Other primary esters can be used in the disclosed processes, such as analogous propionates.

In a particular aspect of this invention, it can be beneficial for the normal alpha olefin to have a boiling point (at a pressure of 1 atm) that is greater than that of the primary ester, i.e., greater than the boiling point (at a pressure of 1 atm) of the primary ester. Generally, the boiling point of the normal alpha olefin can be at least 50° C. greater than that of the primary ester, and in certain aspects, at least 75° C.; alternatively, at least 100° C.; alternatively, at least 150° C.; or alternatively, at least 200° C. (the maximum boiling point difference is not particularly limited, but often can be 350° C., 300° C., 275° C., or 250° C.). For instance, when the normal alpha olefin is 1-tetradecene (251° C. boiling point), 1-hexadecene (285° C. boiling point), or 1-octadecene (315° C. boiling point), the primary ester advantageously can be a lower boiling point primary ester such as methyl acetate (57° C. boiling point) or ethyl acetate (77° C. boiling point). If a low boiling point primary ester is used, then it can be easily removed or separated from the isomerized olefin reaction product using any suitable technique, as discussed further below. For instance, using distillation, the lower boiling point primary ester can be easily removed overhead as a minor component of the isomerized olefin reaction product, and there is no need to distill the heavier mixed olefin component, which is the majority of the isomerized olefin reaction product.

Generally, the appropriate procedure for contacting (or reacting) the olefin feed, the primary ester, and the solid acid catalyst is not particularly limited. For instance, the olefin feed, the primary ester, and the solid acid catalyst can be contacted in any order, manner, or length of time that produces an isomerized olefin reaction product having an acceptable amount of branched olefins and olefin dimers. Nonetheless, in an aspect, the olefin feed and the primary ester can be combined to form a mixture prior to contacting the mixture with the solid acid catalyst.

Certain ratios of components during the isomerization process can prove advantageous with respect to minimizing branched olefins and olefin dimers in the isomerized olefin reaction product. For instance, the minimum amount of the primary ester based on the olefin feed can be at least 1 wt. %, at least 1.5 wt. %, at least 2 wt. %, at least 4 wt. %, or at least 5 wt. %; additionally or alternatively, the maximum amount of the primary ester based on the olefin feed can be less than or equal to 25 wt. %, less than or equal to 20 wt. %, less than or equal to 15 wt. %, or less than or equal to 10 wt. %. Generally, the amount of the primary ester (based on the weight of the olefin feed) can be in a range from any minimum amount disclosed herein to any maximum amount disclosed herein. Accordingly, suitable non-limiting ranges for the amount of the primary ester based on the olefin feed can include the following: from 1 to 25 wt. %, from 5 to 25 wt. %, from 1.5 to 20 wt. %, from 4 to 20 wt. %, from 1 to 15 wt. %, from 2 to 15 wt. %, from 5 to 15 wt. %, from 2 to 10 wt. %, or from 4 to 10 wt. %, and the like.

Likewise, it can be beneficial to conduct the isomerization process in an environment that is substantially free of water/moisture. Thus, all raw materials and the atmosphere for the isomerization process can be dry and substantially free of water/moisture. Thus, aspects of this invention are directed to an isomerization process which is conducted in the presence of less than or equal to 1 wt. % water/moisture, and more often, in the presence of less than or equal to 0.5 wt. %, less than or equal to 1000 ppm (by weight), less than or equal to 500 ppm, or less than or equal to 200 ppm water/moisture, but often greater than 0 ppm, at least 1 ppm, at least 10 ppm, at least 25 ppm, or at least 50 ppm water/moisture.

In an aspect, the isomerization process can be conducted at any temperature below the maximum operating temperature (or thermal stability temperature) of the solid acid catalyst. In another aspect, the isomerization process can be conducted at any temperature below the melting temperature of the solid acid catalyst, or the isomerization process can be conducted at any temperature below the softening point/temperature of the solid acid catalyst. For instance, and depending upon the particular solid acid catalyst, the process can be conducted at a minimum temperature of 10° C., 20° C., 50° C., 70° C., or 80° C.; additionally or alternatively, at a maximum temperature of 180° C., 150° C., 120° C., 110° C., 105° C., or 100° C. Generally, the isomerization temperature can range from any minimum temperature disclosed herein to any maximum temperature disclosed herein. Accordingly, suitable non-limiting ranges for the isomerization temperature and for the formation of the isomerized olefin reaction product can include the following: from 10° C. to 180° C., from 70° C. to 180° C., from 20° C. to 150° C., from 50° C. to 150° C., from 80° C. to 150° C., from 10° C. to 120° C., from 50° C. to 120° C., from 20° C. to 110° C., from 50° C. to 110° C., from 70° C. to 110° C., from 80° C. to 105° C., from 20° C. to 100° C., or from 70° C. to 100° C. These temperature ranges also are meant to encompass circumstances where the isomerization process (or the formation of the isomerized olefin reaction product) is performed at a series of different temperatures, instead of at a single fixed temperature, falling within the respective temperature ranges.

The pressure used for the isomerization process and/or for the formation of the isomerized olefin reaction product is not particularly limited. For instance, the isomerization process can be conducted at an isomerization pressure in a range from 5 psig to 100 psig; alternatively, at atmospheric pressure; or alternatively, at a sub-atmospheric pressure.

In an aspect, the isomerization process can be conducted in a stirred tank reactor. The time period for contacting the olefin feed, the primary ester, and the solid acid catalyst (or for the formation of the isomerized olefin reaction product) in the stirred tank reactor is not particularly limited, and can be conducted for any suitable period of time. Nonetheless, the minimum average residence time in the stirred tank reactor can be 5 min, 10 min, 15 min, 30 min, or 1 hr; additionally or alternatively, the maximum average residence time can be 10 hr, 8 hr, 7 hr, 5 hr, or 3 hr. Generally, the average residence time in the stirred tank reactor for the isomerization process can be in a range from any minimum time disclosed herein to any maximum time disclosed herein. Accordingly, suitable non-limiting ranges for the average residence time can include the following: from 5 min to 10 hr, from 10 min to 8 hr, from 15 min to 7 hr, from 30 min to 5 hr, from 30 min to 3 hr, from 1 hr to 10 hr, from 1 hr to 7 hr, from 1 hr to 5 hr, or from 1 hr to 3 hr.

The weight ratio of the olefin feed to the solid acid catalyst (olefin:catalyst) in the stirred tank reactor is not particularly limited. In an aspect, the isomerization process can be conducted at a minimum weight ratio of olefin:catalyst of at least 1:1, 1.5:1, or 4:1; additionally or alternatively, the isomerization process can be conducted at a maximum weight ratio of olefin:catalyst of less than or equal to 100:1, 40:1, 20:1, or 10:1. Generally, the olefin:catalyst weight ratio can be in a range from any minimum weight ratio disclosed herein to any maximum weight ratio disclosed herein. Accordingly, suitable non-limiting ranges for the olefin:catalyst weight ratio can include the following from 1:1 to 100:1, from 1:1 to 10:1, from 1.5:1 to 40:1, from 1.5:1 to 20:1, from 4:1 to 100:1, from 4:1 to 40:1, or from 4:1 to 20:1.

In an aspect, the isomerization process can be conducted in a fixed bed reactor. In this aspect, the olefin feed-catalyst contact time (or reaction time) can be expressed in terms of weight hourly space velocity (WHSV) the ratio of the weight of the olefin reactant which comes in contact with a given weight of the solid acid catalyst per unit time (units of g/g/hr). While not limited thereto, the isomerization process can be conducted at a minimum WHSV value of 0.05, 0.1, or 0.2; additionally or alternatively, the isomerization process can be conducted at a maximum WHSV value of 5, 2, or 1. Generally, the WHSV can be in a range from any minimum WHSV disclosed herein to any maximum WHSV disclosed herein. Accordingly, suitable non-limiting ranges for the WHSV can include the following: from 0.05 to 5, from 0.2 to 5, from 0.1 to 5, from 0.1 to 2, from 0.1 to 1, from 0.2 to 5, from 0.2 to 2, or from 0.2 to 1.

In some aspects, the isomerization process can include contacting the olefin feed, the solid acid catalyst, the primary ester, and optionally, additional unrecited materials (e.g., a non-olefin solvent or diluent, a stabilizer, amongst other materials). Thus, for example, the isomerized olefin reaction product can be formed in the presence of a non-olefin solvent. The amount of any non-olefin solvent used in addition to olefin feed in the isomerization process is not limited to any particular range. Such solvent, or combination of solvents, can be used, for example, as a flow modifier to alter the flow properties or viscosity of the olefin feed and/or the flow properties of the reaction product. When a non-olefin solvent is used, the isomerization process can be conducted in the presence less than or equal to 25 wt. %, less than or equal to 10 wt. %, or less than or equal to 5 wt. %, and greater than 0 wt. %, at least 0.5 wt. %, at least 1 wt. %, or at least 2 wt. %, of the non-olefin solvent, based on the olefin feed. In some aspects, no additional solvent is used, so a further removal step for the solvent is not needed.

When a non-olefin solvent is used, illustrative non-olefin organic solvents which can be utilized in the process disclosed herein can include alkanes (e.g., pentane, hexane, heptane, octane, cyclohexane), aromatics (e.g., benzene, toluene, xylene, ethylbenzene), halogenated hydrocarbons (e.g., carbon tetrachloride, methylene chloride, chlorobenzene), and the like. Combinations of two or more non-olefin solvents also can be utilized.

The isomerized olefin reaction product can be readily separated from the solid acid catalyst (or the solid acid catalyst can be readily separated from the isomerized olefin reaction product) using any suitable technique, such as filtration.

The isomerization processes disclosed herein typically result in an isomerized olefin reaction product containing the desired isomerized olefin, residual normal alpha olefin and primary ester, branched olefins, and olefin dimers. In many instances, it can be desirable to separate or remove at least a portion (and in some cases, all) of the primary ester from the isomerized olefin reaction product to form a linear internal olefin product. This can be accomplished using any suitable technique, which can include but is not limited to, flashing, wiped film evaporation, distillation, short path distillation, or any combination thereof.

After isomerization (and after removing the primary ester, if desired), the isomerized olefin reaction product (or the linear internal olefin product) can contain minimal amounts of normal alpha olefin and olefin dimer. For instance, the isomerized olefin reaction product (or the linear internal olefin product), based on olefins, can contain less than or equal to 10 wt. %, and more often, less than or equal to 8 wt. %, less than or equal to 5 wt. %, less than or equal to 3 wt. %, or less than or equal to 1 Wt. %, of $C_{10}$ to $C_{20}$ normal alpha olefin, and often can contain greater than 0 wt. %, at least 0.1 wt. %, at least 0.5 wt. %, or at least 0.75 wt. % of $C_{10}$ to $C_{20}$ normal alpha olefin. The isomerized olefin reaction product also can contain an amount of $C_{10}$ to $C_{20}$ normal alpha olefin in a range from any minimum amount disclosed herein to any maximum amount disclosed herein.

Likewise, the isomerized olefin reaction product (or the linear internal olefin product), based on olefins, can contain less than or equal to 10 wt. %, and more often, less than or equal to 7 wt. %, less than or equal to 5 wt. %, less than or equal to 4 wt. %, or less than or equal to 1 wt. %, of dimer (formed from the original $C_{10}$ to $C_{20}$ normal alpha olefin in the olefin feed). Often, this product can contain greater than 0 wt. %, at least 0.1 wt. %, at least 0.5 wt. %, or at least 0.75 wt. % of dimer, based on olefins. The isomerized olefin reaction product (or the linear internal olefin product) also can contain an amount of dimer in a range from any minimum amount disclosed herein to any maximum amount disclosed herein.

Since there is generally some amount of branched olefins in the olefin feed, in addition to the normal alpha olefin, the isomerized olefin reaction product (or the linear internal olefin product) also can contain branched olefins. However, the amount of additional branched olefins over the amount originating in the olefin feed is typically very small. For instance, the isomerized olefin reaction product (or the linear internal olefin product) often contains less than or equal to 10 wt. %, less than or equal to 8 wt. %, less than or equal to 5 wt. %, less than or equal to 3 wt. %, or less than or equal to 2 wt. %, more branched olefins than the amount of branched olefins that were present in the olefin feed, and in some aspects, greater than 0 wt. %, at least 0.1 wt. %, at least 0.5 wt. %, or at least 1 wt. %, more branched olefins than the amount of branched olefins in the olefin feed, and in other aspects, an amount in a range from any minimum amount disclosed herein to any maximum amount disclosed herein.

The isomerized olefin reaction product (or the linear internal olefin product) generally contains, based on olefins, at least 80 wt. % of $C_{10}$ to $C_{20}$ linear internal olefins, and often at least 85 wt. % or at least 90 wt. % of $C_{10}$ to $C_{20}$ linear internal olefins, but typically less than or equal to 99 wt. %, less than or equal to 97 wt. %, or less than or equal to 95 wt. %, of $C_{10}$ to $C_{20}$ linear internal olefins. Additionally or alternatively, the isomerized olefin reaction product (or the linear internal olefin product) can contain an amount of $C_{10}$ to $C_{20}$ linear internal olefins in a range from any minimum amount disclosed herein to any maximum amount disclosed herein. Moreover, the isomerized olefin reaction product (or the linear internal olefin product) can have a nearly equilibrium distribution of linear double bond isomers. Herein, a "nearly equilibrium" distribution of linear double bond isomers means that (a) the amount of 1-alkene is less than or equal to 2 mol % (equivalent to wt. %) determined by FT-IR, and (b) the amount of 2-alkene is less than or equal to 1.25 times the equilibrium level of 2-alkene in mol % (equivalent to wt. %) as determined by GC-FID. The GC-FID procedure is described in the example section below, and the FT-IR procedure determines the mol % of the 1-alkene by 100*(918–899 cm$^{-1}$ area)/(990–930 cm$^{-1}$ area+ 918–899 cm$^{-1}$ area+899–874 cm$^{-1}$ area), where the areas are determined in the IR absorbance spectrum. Table I summarizes the isomer content (mol %) for $C_{12}$ to $C_{20}$ linear olefins at nearly equilibrium distribution. As an example, a mixture of Cis olefins is considered to have a nearly equilibrium distribution of linear double bond isomers if the amount of 1-alkene is less than or equal to 2 mol % and the amount of 2-alkene is less than or equal to 17 mol %.

TABLE I

| Double Bond Position | Isomer Content (mol %) at Near Equilibrium Distribution | | | | |
| --- | --- | --- | --- | --- | --- |
| | C12 | C14 | C16 | C18 | C20 |
| 1 | <1-2 | <1-2 | <1-2 | <1-2 | <1-2 |
| 2 | 22-23 | 18-19 | 15-16 | 13-14 | 11-12 |
| 3 | 22-23 | 18-19 | 15-16 | 13-14 | 11-12 |
| 4 | 22-23 | 18-19 | 15-16 | 13-14 | 11-12 |
| 5 | 22-23 | 18-19 | 15-16 | 13-14 | 11-12 |
| 6 | 11-12 | 18-19 | 15-16 | 13-14 | 11-12 |
| 7 | | 9-10 | 15-16 | 13-14 | 11-12 |
| 8 | | | 7-8 | 13-14 | 11-12 |
| 9 | | | | 6-7 | 11-12 |
| 10 | | | | | 5-6 |
| 1.25 × equilibrium level of 2-alkene | 28 | 23 | 19 | 17 | 15 |

The isomerized olefin reaction product (or the linear internal olefin product) also can contain a minor amount of secondary esters, such as less than or equal to 10 wt. %, less than or equal to 8 wt. %, less than or equal to 5 wt. %, less than or equal to 3 wt. %, or less than or equal to 2 wt. % secondary esters, and in some aspects, greater than 0 wt. %, at least 0.1 wt. %, at least 0.5 wt. %, or at least 1 wt. % secondary esters, and in other aspects, an amount of secondary esters in a range from any minimum amount disclosed herein to any maximum amount disclosed herein. It is unexpected that secondary esters are present in the isomerized olefin reaction product and the linear internal olefin product.

Solid Acid Catalysts

In the isomerization processes disclosed herein, an olefin feed (e.g., any $C_{10}$ to $C_{20}$ normal alpha olefin), a $C_2$ to $C_{15}$ primary ester, and a solid acid catalyst are contacted to form an isomerized olefin reaction product. Any suitable solid acid catalyst can be used. Illustrative and representative examples of suitable solid acid catalysts can include solid acid catalyst resins, such as acidic ion exchange resins. Solid acid catalyst resins can include a styrene-divinylbenzene resin, a functionalized styrene-divinylbenzene resin, a 4-vinylpyridine divinylbenzene resin, a functionalized 4-vinylpyridine divinylbenzene resin, an ionomer resin, a tetrafluoroethylene polymer resin modified with perfluorovinyl ether groups terminated with sulfonate groups, or any combination thereof, alternatively, a styrene-divinylbenzene resin, a 4-vinylpyridine divinylbenzene resin, an ionomer resin, a tetrafluoroethylene resin modified with perfluorovinyl ether groups terminated with sulfonate groups, and the like, as well as combinations thereof; or alternatively, a sulfonated copolymer of styrene-divinylbenzene. Some of these solid acid catalyst types are available under the Amberlyst© resin and Nafion© resin tradenames.

It can be beneficial for the solid acid catalyst used in the isomerization process to be dry and substantially free of water/moisture. The solid acid catalyst often contains less than or equal to 1 wt. % water/moisture, and in some aspects, the water/moisture content of the solid acid catalyst used in the isomerization process can be less than or equal to 0.5 wt. %, less than or equal to 1000 ppm (by weight), less than or equal to 500 ppm, or less than or equal to 200 ppm water/moisture, but often greater than 0 ppm, at least 1 ppm, at least 10 ppm, at least 25 ppm, or at least 50 ppm water/moisture.

Linear Internal Olefin Compositions

A linear internal olefin composition encompassed herein can contain (a) at least 80 wt. % $C_{10}$ to $C_{20}$ linear internal olefins, (b) less than or equal to 8 wt. % $C_{10}$ to $C_{20}$ normal alpha olefin, (c) less than or equal to 8 wt. % dimers of $C_{10}$ to $C_{20}$ olefins, (d) less than or equal to 15 wt. % $C_{10}$ to $C_{20}$ branched olefins, and (e) at least 1 wt. % $C_2$ to $C_{15}$ primary ester and less than or equal to 8 wt. % secondary esters.

Consistent with aspects of this invention, the linear internal olefin composition can contain at least 80 wt. %, at least 85 wt. %, or at least 90 Wt. %, of $C_{10}$ to $C_{20}$ linear internal olefins, and in some aspects, less than or equal to 99 wt. %, less than or equal to 97 wt. %, or less than or equal to 95 wt. %, of $C_{10}$ to $C_{20}$ linear internal olefins, and in other aspects, an amount of $C_{10}$ to $C_{20}$ linear internal olefins in a range from any minimum amount disclosed herein to any maximum amount disclosed herein. Additionally or alternatively, the linear internal olefin composition can contain less than or equal to 8 wt. %, less than or equal to 5 wt. %, less than or equal to 3 wt. %, or less than or equal to 1 Wt. %, of $C_{10}$ to $C_{20}$ normal alpha olefin, and in some aspects, greater than 0 wt. %, at least 0.1 wt. %, at least 0.5 wt. %, or at least 0.75 wt. % of $C_{10}$ to $C_{20}$ normal alpha olefin, and in other aspects, an amount of $C_{10}$ to $C_{20}$ normal alpha olefin in a range from any minimum amount disclosed herein to any maximum amount disclosed herein.

Additionally or alternatively, the linear internal olefin composition can contain less than or equal to 8 wt. % dimers of $C_{10}$ to $C_{20}$ olefins and less than or equal to 15 wt. % $C_{10}$ to $C_{20}$ branched olefins, such as independently less than or equal to 7 wt. %, less than or equal to 5 wt. %, less than or equal to 3 wt. %, or less than or equal to 1 wt. %, of dimer and branched olefins, and in some aspects, greater than 0 wt. %, at least 0.1 wt. %, at least 0.5 wt. %, or at least 1 wt. % respectively of dimer and branched olefins, and in other aspects, an amount of dimer and an amount of branched olefins in a range from any minimum amount disclosed herein to any maximum amount disclosed herein.

Additionally or alternatively, the linear internal olefin composition can contain at least 1 wt. %, at least 1.5 wt. %, at least 2 wt. %, at least 4 wt. %, or at least 5 wt. %, of $C_2$ to $C_{15}$ primary ester, and in some aspects, less than or equal to 25 wt. %, less than or equal to 20 wt. %, or less than or equal to 15 wt. %, of $C_2$ to $C_{15}$ primary ester, and in other aspects, an amount of $C_2$ to $C_{15}$ primary ester in a range from any minimum amount disclosed herein to any maximum amount disclosed herein. Additionally or alternatively, the linear internal olefin composition can contain less than or equal to 8 wt. %, less than or equal to 5 wt. %, less than or equal to 3 wt. %, or less than or equal to 2 wt. % secondary esters, and in some aspects, greater than 0 wt. %, at least 0.1 wt. %, at least 0.5 wt. %, or at least 1 wt. % secondary esters, and in other aspects, an amount of secondary esters in a range from any minimum amount disclosed herein to any maximum amount disclosed herein.

EXAMPLES

The invention is further illustrated by the following examples, which are not to be construed in any way as imposing limitations to the scope of this invention. Various other aspects, modifications, and equivalents thereof, which after reading the description herein, can suggest themselves to one of ordinary skill in the art without departing from the spirit of the present invention or the scope of the appended claims.

Gas Chromatograph (GC) analyses were conducted on an Agilent 7890 GC System, using a HP-Innowax column (polyethyleneglycol, capillary 30 m×0.25 mm×25 m nominal), with 40° C. temperature hold for 2 minutes followed by ramping at a rate of 8° C./min from 40° C. to 220° C., then 15° C./min to 270° C., which is held for 15 minutes. GC analysis column eluents were determined using a flame ionization detector. Standards were used to identify the reactants and products, and to monitor the course of the reactions.

Examples 1-5

1-Tetradecene and Ethyl Acetate

Approximately 2 g of a commercially available 1-tetradecene (~95 wt. % normal alpha olefin and ~5 wt. % vinylidenes/branched olefins) was mixed with ethyl acetate and approximately 7 g decane to form a solution, which was then stirred with 1 g of dry Amberlyst® 15 solid acid catalyst at 90° C. and atmospheric pressure for 3.5 hr. The resulting isomerized olefin reaction product was analyzed using GC for dimers and branched olefins. Table II summarizes the experimental data. The isomerized olefin reaction product of Example 1, in which no ethyl acetate was used, contained 25 wt. % dimers and 18 wt. % branched olefins, based on olefins in the reaction product. Unexpectedly, the addition of ethyl acetate in Examples 2-5, at levels of 2-17 wt. % based on the tetradecene feed, significantly reduced both dimerization and skeletal isomerization. As shown in Table II, both the amount of dimers and the amount of branched olefins decreased as the addition level of ethyl acetate increased. Note that the tetradecene feed contained about 5 wt. % branched olefins, so the reaction products of Examples 3-5 contained less than 2 wt. % more branched olefins than was present in the starting tetradecene feed material.

TABLE II

| Example | ethyl acetate (g) | ethyl acetate (wt. %) | dimers (wt. %) | branched olefins (wt. %) |
| --- | --- | --- | --- | --- |
| 1 | 0 | 0 | 25.4 | 17.8 |
| 2 | 0.05 | 2.4 | 12.4 | 9.1 |
| 3 | 0.10 | 4.7 | 6.4 | 7.0 |
| 4 | 0.20 | 9.1 | 3.7 | 6.2 |
| 5 | 0.41 | 16.9 | 1.6 | 5.7 |

Example 6

1-Octadecene and Ethyl Acetate

A mixture of 93.1 g 1-octadecene (boiling point of 315° C.) and 7.0 g ethyl acetate (boiling point of 77° C.) was stirred with 7.3 g dry Amberlyst® 15 at 90° C. and 300 rpm. The 1-octadecene feed contained approximately 9 wt. % branched olefins. After 119 hr, the isomerized olefin reaction product contained, based on olefins, 0.2 wt. % alpha olefin, 4.9 wt. % dimers ($C_{36}$ olefins), and 11 wt. % branched olefins. Note that the dimers were branched olefins but are not included in the branched olefin content of the reaction product. Of the linear olefins in the reaction product, over 99 wt. % were linear internal octadecenes. The distribution of the internal octadecenes was at nearly equilibrium distribution, as defined hereinabove. Unexpectedly, the reaction product also contained 3.4 wt. % Cis acetates (secondary esters).

Due to the significant difference in boiling point between octadecenes and ethyl acetate, the ethyl acetate can be easily removed from the isomerized olefin reaction product using distillation.

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process for isomerizing olefins, the process comprising contacting (in any order) an olefin feed comprising a $C_{10}$ to $C_{20}$ normal alpha olefin, a solid acid catalyst, and a $C_2$ to $C_{15}$ primary ester, to form an isomerized olefin reaction product.

Aspect 2. The process defined in aspect 1, wherein the olefin feed comprises any $C_{10}$ to $C_{20}$ normal alpha olefin disclosed herein, e.g., a $C_{12}$ to $C_{20}$ normal alpha olefin, a $C_{14}$ to Cis normal alpha olefin, or a $C_{16}$ to Cis normal alpha olefin.

Aspect 3. The process defined in aspect 1 or 2, wherein the olefin feed comprises any $C_{10}$ to $C_{20}$ normal alpha olefin disclosed herein, e.g., 1-decene, 1-dodecene, 1-tetradecene, 1-hexadecene, 1-octadecene, or any combination thereof.

Aspect 4. The process defined in any one of aspects 1-3, wherein the olefin feed comprises any amount of $C_{10}$ to $C_{20}$ normal alpha olefin disclosed herein, e.g., at least 15 wt. %, at least 50 wt. %, at least 70 wt. %, at least 80 wt. %, at least 85 wt. %, or at least 90 wt. %, and less than or equal to 99 wt. %, less than or equal to 97 wt. %, less than or equal to 95 wt. %, or less than or equal to 92 wt. %.

Aspect 5. The process defined in any one of aspects 1-4, wherein the olefin feed comprises any amount of branched olefins disclosed herein, e.g., less than or equal to 12 wt. %, less than or equal to 10 wt. %, less than or equal to 8 wt. %, less than or equal to 6 wt. %, or less than or equal to 5 wt. %, and at least 0.5 wt. %, at least 1 wt. %, at least 2 wt. %, or at least 4 wt. %.

Aspect 6. The process defined in any one of aspects 1-5, wherein the solid acid catalyst comprises any acidic ion exchange resin disclosed herein.

Aspect 7. The process defined in any one of aspects 1-5, wherein the solid acid catalyst comprises any functionalized styrene-divinylbenzene polymer, any 4-vinylpyridine divinylbenzene polymer, or any tetrafluoroethylene polymer modified with perfluorovinyl ether groups terminated with sulfonate groups disclosed herein, as well as combinations thereof.

Aspect 8. The process defined in any one of aspects 1-5, wherein the solid acid catalyst comprises a sulfonated copolymer of styrene-divinylbenzene.

Aspect 9. The process defined in any one of aspects 1-8, wherein the solid acid catalyst comprises any suitable amount of water/moisture, e.g., less than or equal to 1 wt. %, less than or equal to 0.5 wt. %, less than or equal to 1000 ppm, less than or equal to 500 ppm, or less than or equal to 200 ppm, and greater than 0 ppm, at least 1 ppm, at least 10 ppm, at least 25 ppm, or at least 50 ppm.

Aspect 10. The process defined in any one of aspects 1-9, wherein the primary ester comprises methyl acetate, ethyl acetate, n-propyl acetate, n-butyl acetate, pentyl acetate, isoamyl acetate, hexyl acetate, heptyl acetate, octyl acetate, nonyl acetate, decyl acetate, methyl formate, ethyl formate, n-propyl formate, n-butyl formate, pentyl formate, isoamyl formate, hexyl formate, heptyl formate, octyl formate, nonyl formate, decyl formate, or any combination thereof.

Aspect 11. The process defined in any one of aspects 1-10, wherein the normal alpha olefin has a boiling point (at a pressure of 1 atm) greater than that of the primary ester by any amount disclosed herein, e.g., at least 50° C., at least 75° C., at least 100° C., at least 150° C., or at least 200° C.

Aspect 12. The process defined in any one of aspects 1-11, wherein an amount of the primary ester, based on the olefin feed, is in any range disclosed herein, e.g., less than or equal to 25 wt. %, less than or equal to 20 wt. %, less than or equal to 15 wt. %, or less than or equal to 10 wt. %, and at least 1 wt. %, at least 1.5 wt. %, at least 2 wt. %, at least 4 wt. %, or at least 5 wt. %.

Aspect 13. The process defined in any one of aspects 1-12, wherein the process is conducted in the presence of any suitable amount of water/moisture, e.g., less than or equal to 1 wt. %, less than or equal to 0.5 wt. %, less than or equal to 1000 ppm, less than or equal to 500 ppm, or less than or equal to 200 ppm, and greater than 0 ppm, at least 1 ppm, at least 10 ppm, at least 25 ppm, or at least 50 ppm.

Aspect 14. The process defined in any one of aspects 1-13, wherein a mixture of the olefin feed and the primary ester is contacted with the solid acid catalyst.

Aspect 15. The process defined in any one of aspects 1-14, wherein the process is conducted at any isomerization temperature disclosed herein, e.g., from 10° C. to 120° C., from 20° C. to 110° C., from 20° C. to 100° C., from 50° C. to 110° C., from 70° C. to 110° C., or from 80° C. to 105° C.

Aspect 16. The process defined in any one of aspects 1-15, wherein the process is conducted at any isomerization pressure disclosed herein, e.g., from 5 psig to 100 psig, at atmospheric pressure, or at a sub-atmospheric pressure.

Aspect 17. The process defined in any one of aspects 1-16, wherein a weight ratio of the olefin feed to the solid acid catalyst is in any range of weight ratios disclosed herein, e.g., from 1:1 to 100:1, from 1:1 to 10:1, from 1.5:1 to 40:1, or from 4:1 to 20:1.

Aspect 18. The process defined in any one of aspects 1-16, wherein the process is conducted in a fixed bed reactor, and wherein the olefin feed and the solid acid catalyst are contacted at a WHSV in any range of WHSVs disclosed herein, e.g., from 0.05 to 5, from 0.1 to 2, or from 0.2 to 1.

Aspect 19. The process defined in any one of aspects 1-18, wherein the process is conducted in the presence of a non-olefin solvent, and an amount of the non-olefin solvent, based on the olefin feed, is in any range disclosed herein, e.g., less than or equal to 25 wt. %, less than or equal to 10 wt. %, or less than or equal to 5 wt. %, and greater than 0 wt. %, at least 0.5 wt. %, at least 1 wt. %, or at least 2 wt. %.

Aspect 20. The process defined in any one of aspects 1-19, wherein the process further comprises a step of removing all or a portion of the primary ester from the isomerized olefin reaction product to form a linear internal olefin product.

Aspect 21. The process defined in aspect 20, wherein the removing step is performed using any technique disclosed herein, e.g., flashing, wiped film evaporation, distillation, short path distillation, or any combination thereof.

Aspect 22. The process defined in any one of aspects 1-21, wherein the isomerized olefin reaction product (or the linear internal olefin product), based on olefins, comprises any amount of $C_{10}$ to $C_{20}$ normal alpha olefin disclosed herein, e.g., less than or equal to 10 wt. %, less than or equal to 8 wt. %, less than or equal to 5 wt. %, less than or equal to 3 wt. %, or less than or equal to 1 wt. %, and greater than 0 wt. %, at least 0.1 wt. %, at least 0.5 wt. %, or at least 0.75 wt. %.

Aspect 23. The process defined in any one of aspects 1-22, wherein the isomerized olefin reaction product (or the linear internal olefin product), based on olefins, comprises any amount of dimer disclosed herein, e.g., less than or equal to 10 wt. %, less than or equal to 7 wt. %, less than or equal to 5 wt. %, less than or equal to 4 wt. %, or less than or equal to 1 wt. %, and greater than 0 wt. %, at least 0.1 wt. %, at least 0.5 wt. %, or at least 0.75 wt. %.

Aspect 24. The process defined in any one of aspects 1-23, wherein the isomerized olefin reaction product (or the linear internal olefin product) comprises, e.g., less than or equal to 10 wt. %, less than or equal to 8 wt. %, less than or equal to 5 wt. %, less than or equal to 3 wt. %, or less than or equal to 2 wt. %, and greater than 0 wt. %, at least 0.1 wt. %, at least 0.5 wt. %, or at least 1 wt. %, more branched olefins than an amount of branched olefins in the olefin feed.

Aspect 25. The process defined in any one of aspects 1-24, wherein the isomerized olefin reaction product (or the linear internal olefin product) comprises a nearly equilibrium distribution of linear double bond isomers.

Aspect 26. The process defined in any one of aspects 1-25, wherein the isomerized olefin reaction product (or the linear internal olefin product), based on olefins, comprises any amount of $C_{10}$ to $C_{20}$ linear internal olefins disclosed herein, e.g., at least 80 wt. %, at least 85 wt. %, or at least 90 wt. %, and less than or equal to 99 wt. %, less than or equal to 97 wt. %, or less than or equal to 95 wt. %.

Aspect 27. The process defined in any one of aspects 1-26, wherein the isomerized olefin reaction product (or the linear internal olefin product) comprises any amount of secondary esters disclosed herein, e.g., less than or equal to 10 wt. %, less than or equal to 8 wt. %, less than or equal to 5 wt. %, less than or equal to 3 wt. %, or less than or equal to 2 wt. %, and greater than 0 wt. %, at least 0.1 wt. %, at least 0.5 wt. %, or at least 1 wt. %.

Aspect 28. The isomerized olefin reaction product produced by the process defined in any one of aspects 1-27.

Aspect 29. The linear internal olefin product produced by the process defined in any one of aspects 20-27.

Aspect 30. A linear internal olefin composition comprising:
(a) at least 80 wt. % $C_{10}$ to $C_{20}$ linear internal olefins;
(b) less than or equal to 8 wt. % $C_{10}$ to $C_{20}$ normal alpha olefin;
(c) less than or equal to 8 wt. % dimers of $C_{10}$ to $C_{20}$ olefins;
(d) less than or equal to 15 wt. % $C_{10}$ to $C_{20}$ branched olefins; and
(e) at least 1 wt. % $C_2$ to $C_{15}$ primary ester and less than or equal to 8 wt. % secondary esters.

Aspect 31. The composition defined in aspect 30, wherein the composition comprises:
(a) at least 85 wt. % $C_{10}$ to $C_{20}$ linear internal olefins;
(b) less than or equal to 3 wt. % $C_{10}$ to $C_{20}$ normal alpha olefin;
(c) less than or equal to 6 wt. % dimers of $C_{10}$ to $C_{20}$ olefins;
(d) less than or equal to 15 Wt. % $C_{10}$ to $C_{20}$ branched olefins; and
(e) at least 2 wt. % $C_2$ to $C_{15}$ primary ester and less than or equal to 5 wt. % secondary esters.

I claim:
1. A process for isomerizing olefins, the process comprising contacting:
(i) an olefin feed comprising a $C_{10}$ to $C_{20}$ normal alpha olefin;
(ii) a solid acid catalyst resin; and
(iii) a primary ester comprising ethyl acetate;
to form an isomerized olefin reaction product.

2. The process of claim 1, wherein the olefin feed comprises 1-decene, 1-dodecene, 1-tetradecene, 1-hexadecene, 1-octadecene, or any combination thereof.

3. The process of claim 1, wherein the olefin feed comprises:
at least 85 wt. % $C_{10}$ to $C_{20}$ normal alpha olefin; and
less than or equal to 10 wt. % branched olefins.

4. The process of claim 1, wherein the normal alpha olefin has a boiling point that is at least 50° C. greater than that of the primary ester.

5. The process of claim 1, wherein the solid acid catalyst resin comprises a functionalized styrene-divinylbenzene polymer, a 4-vinylpyridine divinylbenzene polymer, or a tetrafluoroethylene polymer modified with perfluorovinyl ether groups terminated with sulfonate groups, or any combination thereof.

6. The process of claim 1, wherein the solid acid catalyst resin comprises a sulfonated copolymer of styrene-divinylbenzene.

7. The process of claim 1, wherein the solid acid catalyst resin contains less than or equal to 1 wt. % of water/moisture.

8. The process of claim 1, wherein an amount of the primary ester, based on the olefin feed, is from 1 to 25 wt. %.

9. The process of claim 1, wherein the process is conducted in a stirred tank reactor at a weight ratio of the olefin feed to the solid acid catalyst resin in a range from 1:1 to 100:1.

10. The process of claim 1, wherein the process is conducted in a fixed bed reactor at an olefin feed WHSV in a range from 0.05 to 5.

11. The process of claim 1, wherein the isomerized olefin reaction product comprises, based on olefins:
at least 85 wt. % of $C_{10}$ to $C_{20}$ linear internal olefins;
less than or equal to 3 wt. % of $C_{10}$ to $C_{20}$ normal alpha olefin; and
less than or equal to 7 wt. % of dimer.

12. The process of claim 1, wherein the process further comprises a step of removing all or a portion of the primary ester from the isomerized olefin reaction product to form a linear internal olefin product.

13. The process of claim 12, wherein the removing step comprises flashing, wiped film evaporation, distillation, short path distillation, or any combination thereof.

14. The process of claim 12, wherein the linear internal olefin product comprises, based on olefins:
at least 80 wt. % of $C_{10}$ to $C_{20}$ linear internal olefins;
less than or equal to 5 wt. % of $C_{10}$ to $C_{20}$ normal alpha olefin; and
less than or equal to 10 wt. % of dimer.

15. The process of claim 14, wherein the linear internal olefin product further comprises:
less than or equal to 8 wt. % of secondary esters; and
less than or equal to 5 wt. % more branched olefins than an amount of branched olefins in the olefin feed.

16. The process of claim 12, wherein the linear internal olefin product comprises, based on olefins:
- at least 85 wt. % of $C_{10}$ to $C_{20}$ linear internal olefins;
- less than or equal to 3 wt. % of $C_{10}$ to $C_{20}$ normal alpha olefin; and
- less than or equal to 5 wt. % of dimer.

17. The process of claim 16, wherein the linear internal olefin product comprises a nearly equilibrium distribution of linear double bond isomers.

18. The process of claim 1, wherein:
- the olefin feed comprises at least 80 wt. % $C_{12}$ to $C_{20}$ normal alpha olefin and less than or equal to 12 wt. % branched olefins.

19. The process of claim 18, wherein the normal alpha olefin has a boiling point that is from 75 to 250° C. greater than that of the primary ester.

20. The process of claim 18, wherein an amount of the primary ester, based on the olefin feed, is from 2 to 20 wt. %.

21. The process of claim 20, wherein the solid acid catalyst resin comprises a sulfonated copolymer of styrene-divinylbenzene.

\* \* \* \* \*